(12) United States Patent
Sollboehmer et al.

(10) Patent No.: US 7,455,815 B2
(45) Date of Patent: Nov. 25, 2008

(54) MICRO-TITRE PLATE OR CHIP WITH AN EMBEDDED SUPPORT CORE

(75) Inventors: Olaf Sollboehmer, Hamburg (DE); Ahmet Kabakci, Istanbul-Bebek (TR)

(73) Assignee: Evotec AG, Hamburg (DE)

( * ) Notice: Subject to any disclaimer, the term of this patent is extended or adjusted under 35 U.S.C. 154(b) by 415 days.

(21) Appl. No.: 10/312,640

(22) PCT Filed: Jun. 2, 2001

(86) PCT No.: PCT/EP01/06327

§ 371 (c)(1),
(2), (4) Date: Feb. 18, 2003

(87) PCT Pub. No.: WO01/94018

PCT Pub. Date: Dec. 13, 2001

(65) Prior Publication Data

US 2003/0157701 A1    Aug. 21, 2003

(30) Foreign Application Priority Data

Jun. 7, 2000  (DE)  ............................... 100 28 323

(51) Int. Cl.
| | |
|---|---|
| *B01L 3/00* | (2006.01) |
| *B32B 3/00* | (2006.01) |
| *B32B 37/00* | (2006.01) |
| *F17C 3/00* | (2006.01) |
| *C12M 3/00* | (2006.01) |

(52) U.S. Cl. .................. 422/102; 428/156; 220/560.05; 435/303.1; 156/39

(58) Field of Classification Search ................ 422/101, 422/102; 428/156; 156/73.1, 39; 220/560.05; 435/303.1
See application file for complete search history.

(56) References Cited

U.S. PATENT DOCUMENTS

| | | | | |
|---|---|---|---|---|
| 3,399,111 A | * | 8/1968 | Beaumont et al. ............ | 162/199 |
| 4,810,321 A | * | 3/1989 | Wank et al. ............ | 156/244.23 |
| 4,948,442 A | * | 8/1990 | Manns ........................ | 156/73.1 |
| 5,241,363 A | * | 8/1993 | Garner ........................ | 356/326 |

(Continued)

FOREIGN PATENT DOCUMENTS

EP    0 844 025    5/1998

(Continued)

OTHER PUBLICATIONS

Kinetics, Inc., Precision Problem-Solving through Metal Injection Molding, Jan. 15, 1998, p. 1.*

*Primary Examiner*—Jill Warden
*Assistant Examiner*—Lore Ramillano
(74) *Attorney, Agent, or Firm*—Ohlandt, Greeley, Ruggiero & Perle, L.L.P.

(57) ABSTRACT

A sample support, which is configured in the form of a titre plate or chip, has a plastic support plate and several recesses for receiving samples. Said recesses are sealed with a glass plate. According to the present disclosure, a support core surrounding the recesses is embedded in the support plate in order to prevent contraction during the process for producing the support plate. The support core is preferably a metal plate with areas which have not been extrusion-coated, for use as contact surfaces. Heat can be introduced into the titre plate through these contact surfaces.

9 Claims, 4 Drawing Sheets

U.S. PATENT DOCUMENTS

| | | | | |
|---|---|---|---|---|
| 5,504,007 | A | * | 4/1996 | Haynes .................... 435/285.1 |
| 5,846,396 | A | * | 12/1998 | Zanzucchi et al. ............ 506/33 |
| 5,849,208 | A | * | 12/1998 | Hayes et al. .................. 216/94 |
| 5,858,653 | A | * | 1/1999 | Duran et al. .................... 435/6 |
| 5,961,932 | A | * | 10/1999 | Ghosh et al. ................ 422/193 |
| 6,074,614 | A | * | 6/2000 | Hafeman et al. ............ 422/102 |
| 6,136,592 | A | * | 10/2000 | Leighton ................. 435/288.7 |
| 6,340,589 | B1 | * | 1/2002 | Turner et al. ............. 435/287.2 |
| 6,485,690 | B1 | * | 11/2002 | Pfost et al. .................. 422/102 |
| 6,613,285 | B1 | * | 9/2003 | Carnahan .................... 422/102 |
| 6,676,905 | B2 | * | 1/2004 | Al-Obeidi et al. ........... 422/102 |
| 2004/0209392 | A1 | * | 10/2004 | Craighead et al. ............. 438/48 |

FOREIGN PATENT DOCUMENTS

| | | |
|---|---|---|
| JP | 07125739 | 5/1995 |
| WO | WO 99/19717 | 4/1999 |

* cited by examiner

MICRO-TITRE PLATE OR CHIP WITH AN EMBEDDED SUPPORT CORE

FIELD OF THE DISCLOSURE

The present disclosure refers to a sample support for receiving biological and/or chemical samples comprising a flat support plate with a plurality of recesses. These form individual receptacles in the support plate serving to receive samples.

The sample support is a titre plate, for example. The same usually comprises a support plate with continuous recesses closed by a bottom plate, a glass plate, for example.

DISCUSSION OF THE RELATED ART

In titre plates, the individual recesses are spaced regularly in the support plate so as to fill samples into the individual recesses using an automated process and to automatically examine these samples thereafter. In particular, the samples received in the recesses are micro-samples of a volume less than 1 µl. When filling the recesses automatically and when examining the samples automatically, particularly the mutual distances between the individual recesses have to be defined exactly, since the titre plate must be moved with a fixed step size towards a pipette or a measuring objective, for example. With correspondingly small recesses in the titre plate, the tolerances of the support plate have to be smaller than ±100 µm to realize an automatic process. In particular for an optical analysis of the samples, a high degree of planarity is further required. The tolerable unevenness of the support plate is less than 200 µm.

The support plates of conventional titre plates are often made from chemically inert plastic material such as polypropylene. Thereafter, the support plate is provided with the bottom plate in order to close the continuous recesses in the support plate. The bottom plate may be a glass plate or a transparent plastics foil, for example. Support plates of plastic material are disadvantageous in that plastic material shrinks while cooling. As a consequence, the dimensional accuracy of the support plate often falls outside the tolerance range. Since the degree of shrinking is particularly dependent on environmental conditions during the production process, such as the air humidity, for example, the degree of shrinking varies so that the shrinking cannot be compensated by simply adding material.

Further, the sample supports may be chips. Typically, the recesses in chips are one or a plurality of channels that could be capillary channels and, possibly, one or a plurality of liquid reservoirs. For example, these may be micro-fluidic chips preferably comprising two reservoirs interconnected by a channel. Fluid exchange occurs between both reservoirs that may be controlled through appropriate valves, membranes, osmotic barriers and/or ion barriers. With such chips, the mixing behavior of liquids, e.g., under the influence of electromagnetic forces may be studied. Known chips are made of silicon or glass. Due to the strong shrinking behavior of plastic material, chips cannot be made with sufficient accuracy from plastic material.

Further, chips may have a plurality of inlet channels, as well as a channel array for receiving and/or guiding fluids, suspensions or solutions, one or a plurality of outlet channels and a plurality of reservoirs. The reservoirs may hold a treatment solution for washing, cultivating, preserving, cryo-preserving etc. Further, the chips could comprise pump devices such as peristaltic pumps, spray pumps or electro-osmotic fluid and particle drives. In addition, sensors for determining sample properties, such as temperature, pH value or conductivity, may be provided.

Moreover, chips of silicone material, especially silicone rubber, are known that are cast at ambient temperature, cure and are removed from the form after curing. These silicon chips can be used directly after removal from the form. Due to the process, no or only very little shrinking occurs. However, silicon chips can be produced only in relatively large structural sizes. It is not possible to produce channel dimensions of less than 10 nm in silicon chips.

Further, silicon chips have the disadvantage that larger cavities deform due to the dead weight of the walls.

SUMMARY OF THE DISCLOSURE

It is the object of the present disclosure to improve the dimensional accuracy of a sample support and, in particular, the planarity of titre plates.

According to the present disclosure, a support core is embedded in the support plate of the sample support, which core surrounds the recesses of the support plate. The support core is made of a material with a higher melting point than the plastic material of the support plate. When manufacturing the support plate, for example by injection molding a plastics layer, preferably of polypropylene or silicon, around the support core, the support core is surrounded by the plastics layer. The support core is entirely enclosed by the plastics layer at least in the area of the recesses in the support plate. Due to the provision of a support core that does not melt during manufacture, the plastics layer is substantially thinner than in conventional support plates. As a result, a lesser contraction occurs. The present sample support thus is considerably more dimensionally accurate so that it is possible to observe even small tolerances.

Providing a support of a material with a higher melting temperature is further advantageous in that the stability of the sample support is increased. Therefore, the sample support is not as easily deformed during automatic analysis procedures as known titre plates are, for example. This is advantageous in that the positions of the individual recesses of the sample support are not disturbed by the action of external forces.

Providing a chip with a support core, as in the present disclosure, it becomes possible to manufacture chips from plastic material, since a sufficient dimensional accuracy can be obtained. This is advantageous in that the plastic material used can be polypropylene which is preferred for its chemical inertness. The present structure of a plastic material chip with a higher-melting core provides for an unbreakable chip. Substantial advantages for handling are obtained thereby, in particular in automated processes. Even if the core is made of fragile material, the same is sufficiently protected by the plastic material sheath.

Further, according to the disclosure, providing a support core of higher-melting material it also becomes possible to produce silicon chips since the support core increases the stability of the silicon, in particular the silicon rubber, so that the chip structure will no longer be deformed by its own weight. Furthermore, the support core avoids a deformation of the present chip during manual or automatic handling.

With conventional titre plates, strong stresses occur upon temperature variations since the thermal dilatation coefficients of the plastic material of the support plate and the glass of the bottom plate, for example, differ. This causes deformations in the titre plate. According to the present disclosure, the thermal dilatation coefficient of the support core may be selected such that it corresponds to or is similar to the thermal dilatation coefficient of the bottom plate. Thus, the stresses caused in the titre plate by temperature variations are substantially reduced. For example, this is also true for thermal stresses that occur when a film serving as the bottom plate is fastened to the support plate by welding.

Preferably, each recess of the support plate is enclosed by the support core. Thus, the shrinking of the support plate while cooling is further reduced.

The support core may, e.g., be a plaiting or a net of hard plastic material or metal. The support core may comprises glass, semiconductors, in particular silicon, doped silicon, ceramics or doped ceramics. Such cores are particularly advantageous with chips. Preferably, the support core is a metal plate. The metal plate has openings corresponding to the recesses in the support plate. For example, this is necessary for titre plates, since the recesses extend through the entire support plate and are therefore not interrupted by the support core. With chips, the support core may be designed such that it is present both laterally beside and beneath the recess.

The dimensions of the openings in the support core are preferably slightly larger that the recesses of the support plate. Thus, a very thin wall thickness of the recesses can be obtained so that the plastic material of the support plate is subjected to no or only extremely little contraction in this portion in particular. Preferably, the wall thickness of the recesses is 0.1-0.7 mm. A wall thickness of 0.2-0.5 mm is most preferred.

In a particularly preferred embodiment, a thermally conductive core, e.g., a metal plate, is embedded in the support plate. In this embodiment, the support core has exposed contact surfaces, i,e. regions that are not enclosed by the plastic material of the support plate. Through these contact surfaces heat may be introduced into the titre plate and/or dissipated therefrom. Thus, a simple and purposeful heating or cooling the sample support is possible. In particular, it is possible to impart a temperature gradient to the sample support so that a sample support can be heated or cooled over a predetermined course of time. Along its length, the sample support may be given a temperature varying, e.g., in the longitudinal direction. The heating of the sample support may, e.g., be effected by coupling in eddy currents or by contact between heating elements and the contact surfaces. Both for heating and for cooling, the present titre plate does not have to be disposed in a closed housing and there is no need to heat or cool the entire inner space of this housing.

Providing a metal support core is further advantageous in that the same may be magnetic or magnetizable. Thus, it is possible, e.g. via the contact surfaces, to move the sample support by means of a magnetic gripper in an automatic examination process. Similarly, a sample support can be moved in a simple manner using magnet conveyor systems. This is advantageous uin that the sterility of the sample support is improved, since the transport requires no contact with the sample supports. Further, such sample supports allow for the provision of a magnetic cover system.

Providing the support core according to the disclosure, the sample support can be realized with a high-quality planar surface. Thus, it is possible to use suction cups for transporting the sample supports. In this case, transporting is effected with a vacuum applied to the suction cups.

For transporting purposes, the sample support may comprise projections of prism-like sectional shape, preferably provided in the edge portion of the sample support. The prism-shaped projections automatically center the sample support in a correspondingly designed gripper. Similarly, the sample support may have spherical recesses into which spheres of the gripper engage. Again, this causes an automatic centering.

When the sample support is a titre plate, the same may also be integrally formed. Here, it is possible, e.g. in a single injection molding process, to inject the plastic material around the support core while simultaneously forming the support plate and the bottom plate.

To avoid shrinking of thick sample supports, these are preferably provided with a plurality of substantially parallel plates as the support core. Preferably, these are metal plates as well. In particular, they could be arranged in the form of a sandwich structure so that the plastic nmaterial of the sample support or another material is provided between the individual plates of the support core. Here, it is also possible to provide a material with an appropriate thermal dilatation coefficient between the individual plates so as to avoid stresses in the sample support.

In order to produce the above-described sample support, the support core is preferably extrusion-coated with plastic material, preferably polypropylene, so that a support plate with an embedded support core is obtained. Here, the support core is completely surrounded by the plastic material in the region of the recesses of the support plate. Depending on the respective embodiment, surrounding plastic material is not required in adjacent regions or it is not desired, if contact surfaces are provided. When the sample support is a titre plate, the bottom plate is subsequently fastened to the support plate.

When the bottom plate is a glass plate, it is preferably glued. When plastic material films are used as the bottom plate, the fastening is preferably done by welding.

Preferably, the manufacture is effected through extrusion-coating, the support core being placed in an injection mold prior to extrusion-coating.

When the support core is a metal plate, it is preferably made by punching.

The following is a detailed description of preferred embodiments of the invention with reference to the accompanying drawings.

DETAILED DESCRIPTION OF THE DISCLOSURE

Figure 1:
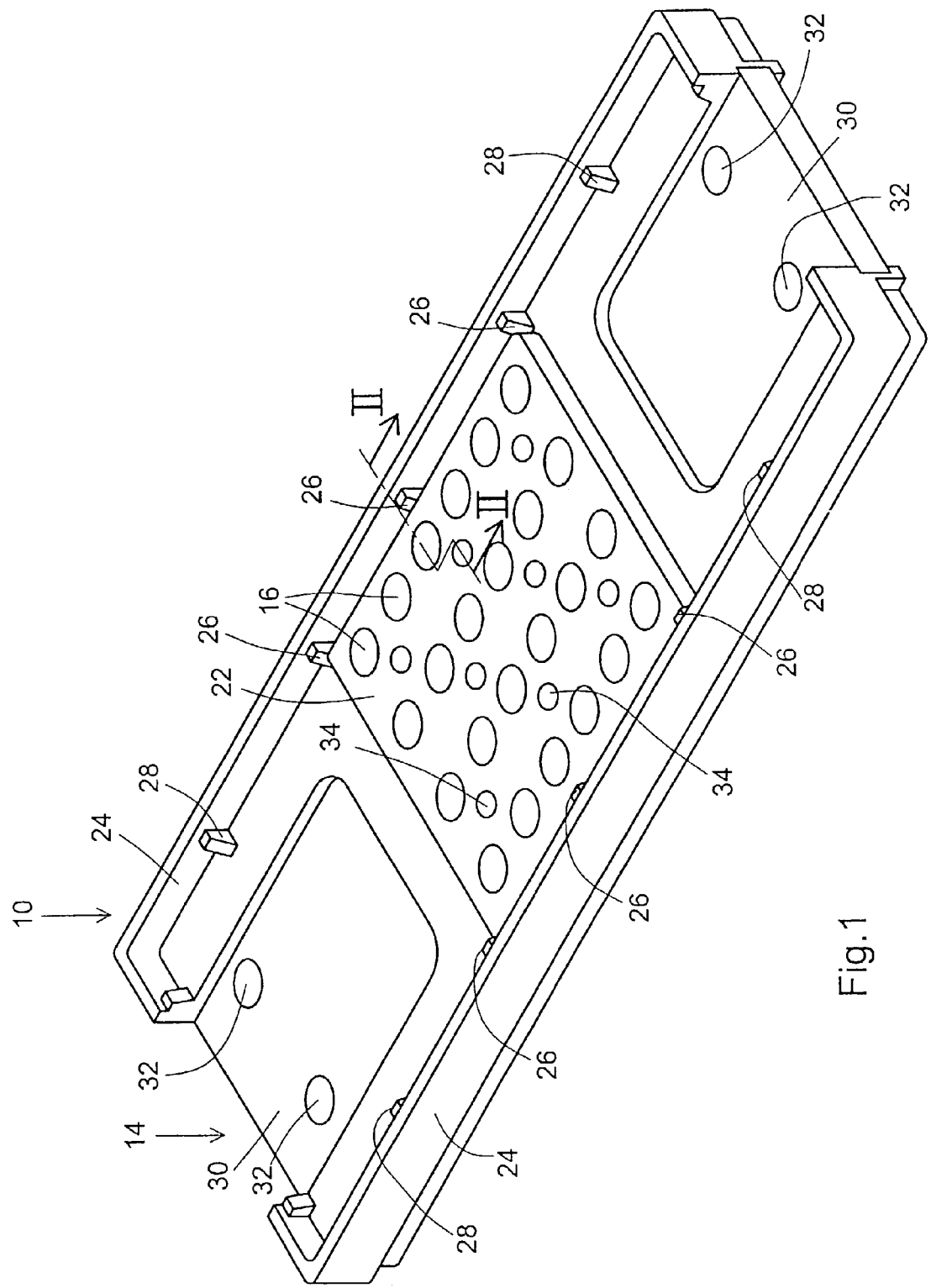
FIG. 1 is a schematic perspective view of a preferred embodiment of the sample support from below and without bottom plate.

The support plate 10 illustrated in FIG. 1 is illustrated without a bottom plate 12 (FIG. 2) which may be a glass plate, for example. The support plate 10 comprises a support core 14 embedded therein and having the form of a metal plate. The length of the metal plate 14 is the same as that of the support plate 10. In the central portion of the support plate 10, recesses 16 for receiving samples are provided. The recesses 16 extend over the entire height of the support plate 10. Thus, they are continuous recesses.

Accordingly, the metal plate 14 comprises openings 18 (FIG. 2) corresponding to the recesses 16. The diameter of the circular openings 18 is slightly larger than the diameter of the recesses 16. Thereby, the recesses 16 have a thin wall 20 in the region of the metal plate 14. The recesses 16 as well as the corresponding openings 18 may also have another shape, e.g. an octagonal shape. Similarly, the recesses 16 and the openings 18 may be conically shaped. In this case, the wall thickness of the wall 20 is possibly almost uniform.

The recesses 16 are regularly disposed. In the embodiment illustrated there are four rows with six recesses 16 each so that the illustrated embodiment of the titre plate has twenty-four recesses. Other usual formats comprise 96, 384, 1536, 2080 and 3456 recesses, for example. All recesses 16 have the same diameter.

To close the recesses 16, a glass plate 12 is located on the surface 22. The glass plate 12 is mounted on the surface 22 by glueing, for example. For an exact positioning of the glass plate 12, the frame portions 24 provided at the longitudinal edges of the support plate 10 are formed with projections 26. Thus, a slipping of the glass plate 12 during glueing is avoided so that the glass plate cannot be contaminated by adhesive in the region of the recesses 16.

The height of the frame portions 24 is chosen such that the frame portions 24 project beyond the glass plate even when the same is glued therein. This allows for a stacking of a plurality of titre plates without one glass plate 12 contacting a subjacent titre plate and without being damaged thereby. For a lateral guiding of stacked titre plates, the face opposite the frame portions 24, i.e. the top surface of the titre plates, have a smaller width so that upon stacking the individual titre plates slip into each other. In addition to the projections 26 between which the glass plate 12 is located projections 28 are provided to avoid contact with the glass plate 12. With stacked titre plates, the adjacent titre plate rests on the top surfaces of the projections 26 and 28, respectively.

The support core 14 extending over the entire length of the support plate 10 is not entirely extrusion-coated with plastic material, but has a contact surface 30 at both end portions. Through the contact surface 30, heat may be induced into the metal plate 14 to heat the samples in the recesses 16. To fix the position of the titre plate in a device, additional aligning bores 32 are provided in the contact surfaces 30.

Figure 2:
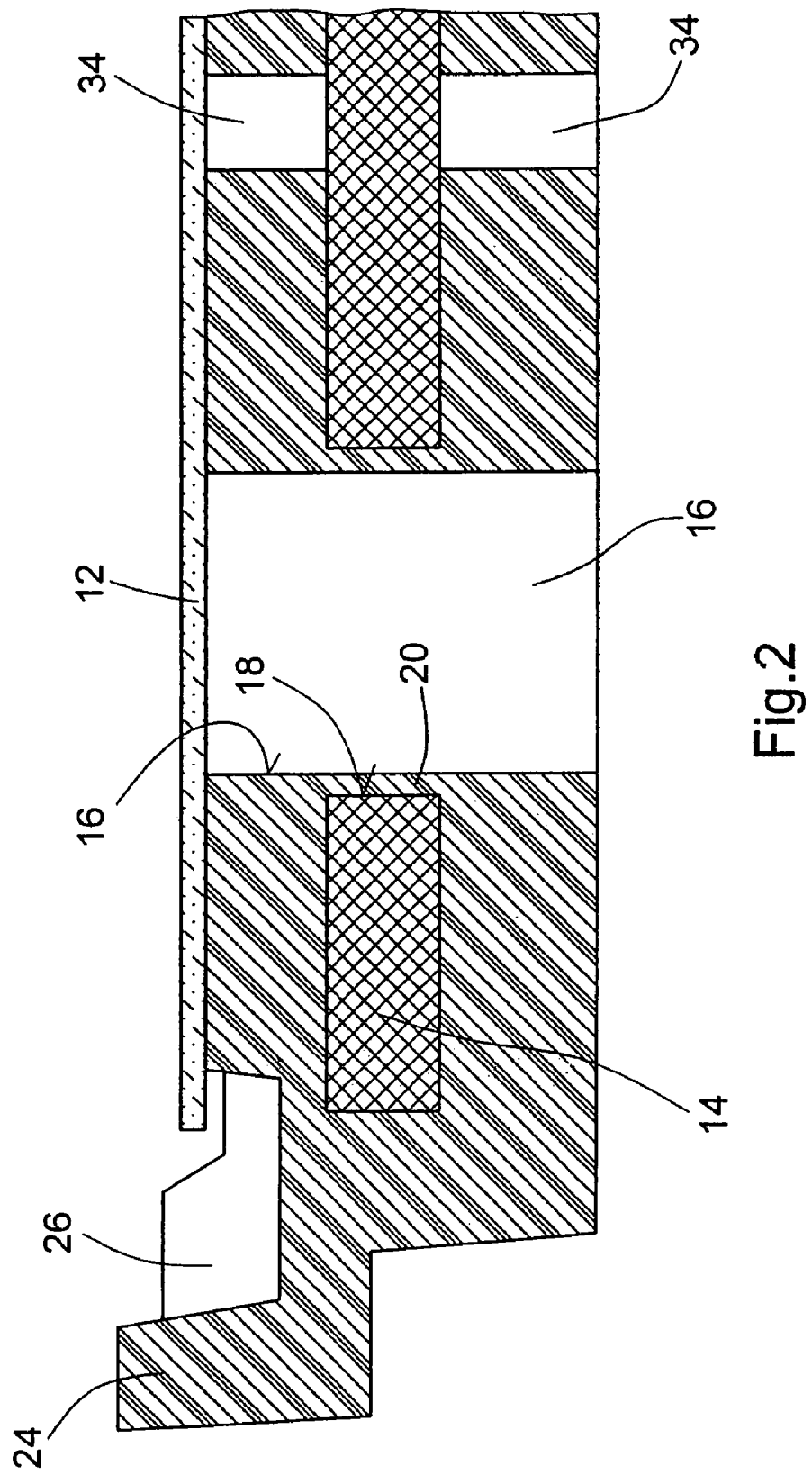
FIG. 2 is a sectional view along line II-II in FIG. 1 with the bottom plate provided.

Further, the support plate 10 has homogenizing recesses 34 in the area of the recesses 16. The homogenizing recesses 34 are arranged between the recesses 16 such that each recess 15 is adjacent at least one homogenizing recess 34. The homogenizing recesses 34 do not extend through the entire support plate. This means that the metal plate has no corresponding openings (FIG. 2). The homogenizing openings 34 illustrated in FIG. 1 are associated with a respective further opposite homogenizing recess 34. In particular when heating the titre plate, the homogenizing recesses 34 compensate for dilatation of the plastic material of the support plate. Further, the support plate may be ejected from the injection molding tool at these locations by means of an ejector, the ejecting also being possible by retracting the ejectors. Further, the ejectors stabilize the core in the injection molding mold.

Additionally, the metal plate 14 has openings beside the area where the openings 16 or the corresponding openings 18 are provided, which openings are entirely filled with plastic material when extrusion-coating the metal plate 14. These openings serve to positively fix the plastic material sheath to the metal plate 14.

Further, the metal plate 14 may have retaining bores. These are blind bores or throughbores. Since plastic material enters the retaining bores upon extrusion-coating the metal plate 14, a positive connection between the metal plate and plastic material is obtained. A positive connection may also be effected by providing impressions or other indentations in the metal plate 14. Similarly, the metal plate may comprise projections which will then be extrusion-coated with plastic material. These also form a positive connection between the metal plate and the plastic material. In addition or instead of the retaining bores, the top surface of the metal plate 14 may be roughened. This results in a better connection between the plastic material and the metal plate 14.

Figure 3:
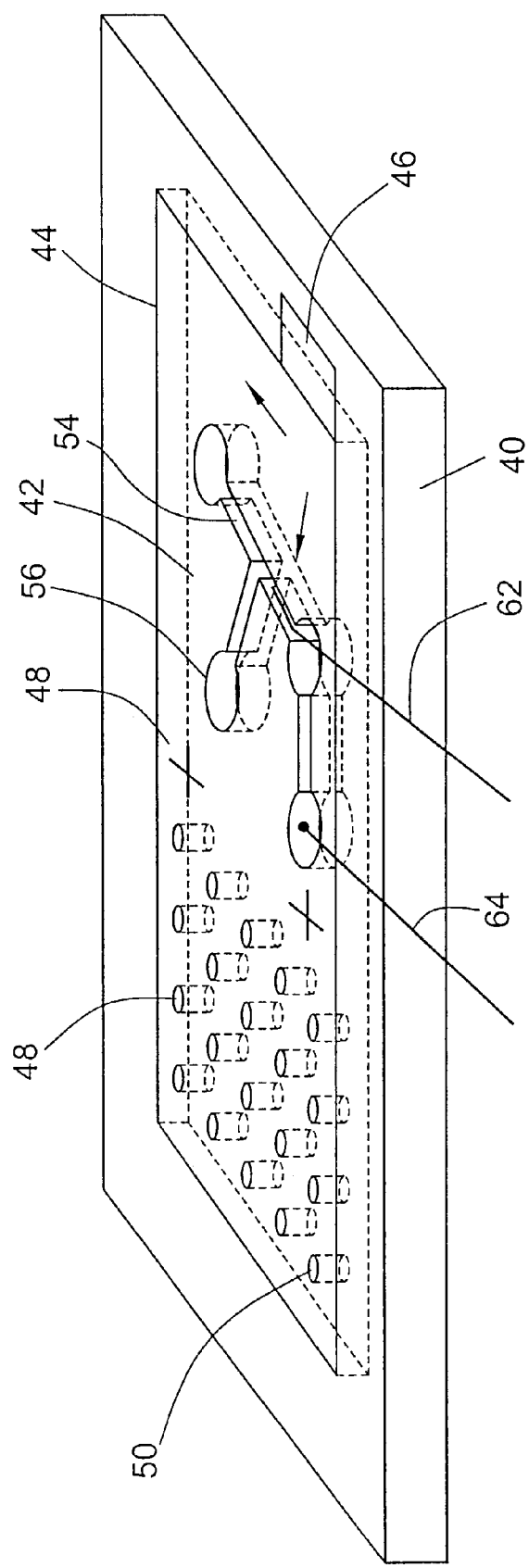
FIG. 3 is a schematic perspective view of a chip.

FIG. 3 is a schematic perspective view of a chip structure. Different compartment structures and additional means are shown on the sample support which, depending on the respective application, may be provided individually or simultaneously. The chip structure comprises the bottom part or the frame 40 and the sample support 42.

The bottom part 40 is a planar glass plate, for example, having a thickness corresponding to the thickness of cover glasses used in microscopy (about 150 μm). The bottom part 40 may also be formed by any other body with a substantially smooth, planar or curved surface. Preferably, the bottom part has a substantially smooth planar surface.

The sample support 42 comprises, e.g., a compartment layer 44 with compartment structures. The compartment layer 44 preferably consists of silicone rubber. One or a plurality of sides of the compartment layer may be provided with a tab 46 for pulling off the sample support 42 from the bottom part 40 and/or aligning marks 47 for positioning the sample support 42 relative to a measuring or sample supply means. The aligning marks 47 may, e.g., be point-shaped or cross-shaped recesses in the surface of the sample support 42 that may possibly be provided with an additional marker substance (e.g. a fluorescent color). The aligning marks have characteristic dimensions that are substantially smaller than the dimensions of the compartment structures can be.

In correspondence to the titre plate described with reference to FIGS. 1-2 and according to the disclosure, the sample support 42 comprises a core of higher-melting material.

Specifically, the compartment structures comprise closed sample reservoirs 48 in the form of continuous holes 50 or of indentations sunk into the surface of the sample support (diameter approx. 200 μm to 1,5 mm, for example) or straight, curved or branched channels 54 extending in the plane of the layer of the sample support. The reference numeral 56 refers to so-called supply pots that are designed to receive and discharge samples just like the sample reservoirs 48, however, with a larger volume.

The manipulation and examination means may comprise a fluid line, for example, in the form of at least one capillary 54, at least one electrode 62 and/or at least one sensor 64 arranged in the layer plane of the sample support 42, at the walls of the compartment structures or in the compartment structures. The capillary 54 may, for example, be connected to a sample or reagent supply system (not illustrated). During the manufacture of the sample support 42 (see below), it is embedded in the same or posteriorly pierced into the sample support 42. The electrodes are constructed as is known per se from micro system technology for microelectrodes for electro-osmotic pumping operations, manipulations of particles using negative dielectrophoresis or particle treatment such as, for example, electroporatoion of biological cells. The electrodes or their supply lines are preferably embedded into the sample support 42 or arranged on the inner surfaces (walls of the compartment) thereof during the manufacture of the sample support.

Figure 4:
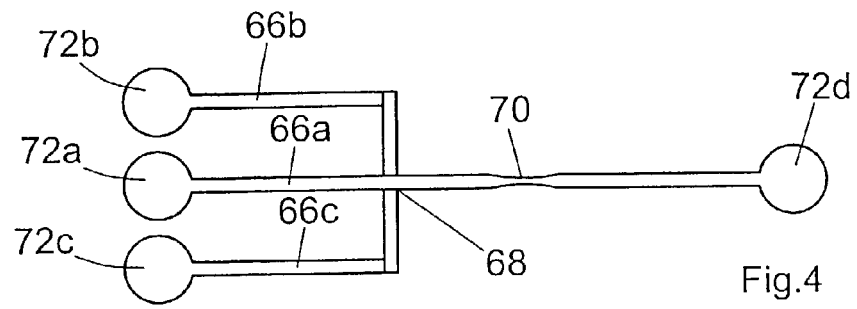
FIGS. 4 to 7 are examples of different chip structures.

FIG. 4 illustrates a channel structure with a plurality of channels 66a-66c connected at a mixing node 68. At the channel ends, respective supply pots 72a-72d are provided. Reference numeral 70 designates a constriction. The constriction 70 may be formed flow-mechanically by barriers (bulging channel wall) or electrically by electric field barriers, to delay the fluid flow upstream of this portion and to take measurements of suspended particles in the fluid flow, for example.

Figure 5:
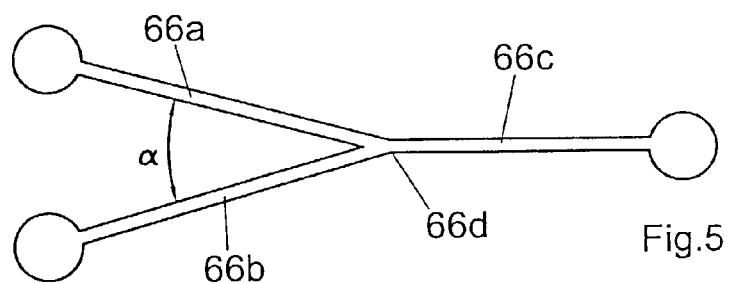

A variant is illustrated in FIG. 5. Two partial channels 66a, 66b merge into a common channel 66c. This structure serves to mix two fluid flows to a single fluid flow. The angle α between the partial channels 66a, 66b is set depending on the application to obtain a uniform flow at the mixing point 66d.

Figure 6:
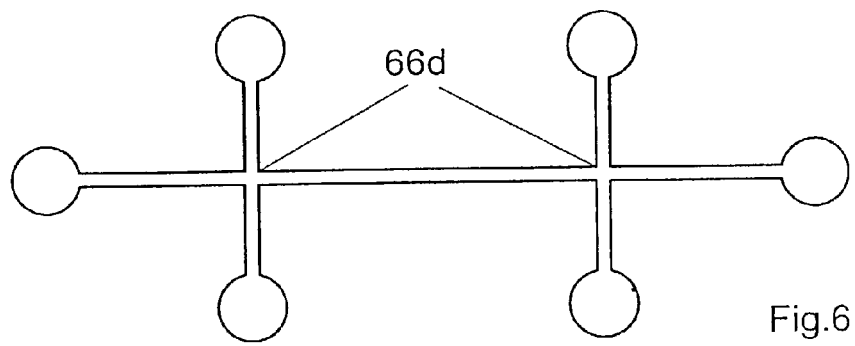
Figure 7:
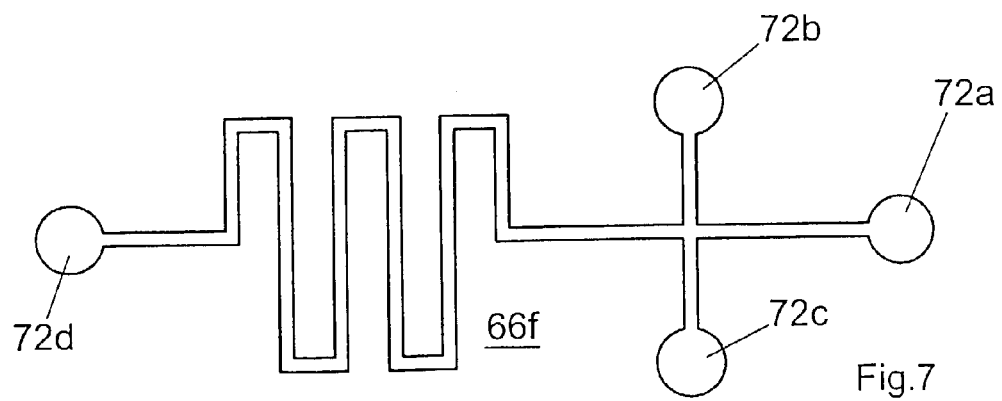

Another variant of structures for mixing fluid flows is illustrated in FIG. 6 as a double cross arrangement with a plurality of partial channels terminating at to mixing points 66d. The meander shape 66f of FIG. 7 serves to provide a particularly long measuring path. Between the supply pots 72a-72d on the one hand and the supply pot 72d, a long and winding channel extends in a surface portion that could be an illumination target for fluorescence measurements.

Like the titre plate described with reference to FIGS. 1 and 2 and according to the disclosure, the chip structures illustrated as examples and the chip illustrated in FIG. 3 also comprise a core of higher-melting material. As with the titre plates, the same reduces the occurrence of contractions. In FIG. 3, the sample support 42 comprises a non-illustrated core of metal or higher-melting material. In this case, the metal core is entirely extrusion-coated with plastic material.

The invention claimed is:

1. A sample support for receiving biological and/or chemical samples, comprising:
   a flat support plate of plastic material comprising a plurality of recesses, wherein a support core of a higher-melting material is embedded in said flat support plate, said support core surrounding said recesses,
   wherein said support core is entirely enclosed by said plastic material at least in the area of said recesses of said support plate, and wherein said support core is a metal plate with openings corresponding to said recesses, wherein the diameter of said openings are larger than the diameter of said recesses.

2. The sample support of claim 1, wherein the dimensions of said openings of said support core are larger than those of said recesses of said support plate, wherein the wall thickness of said recesses is in the range between about 0.1 to 0.7 mm.

3. The sample support of claim 2, wherein said wall thickness of said recesses is in the range between about 0.2 to 0.5 mm.

4. The sample support of claim 1, wherein said support core has at least one exposed contact surface.

5. The sample support of claim 1, wherein said sample support is designed as a titre plate, said recesses in said support plate being continuous, and a bottom plate closing said recesses is provided.

6. The sample support of claim 5, wherein said support plate and said bottom plate are integral.

7. The sample support of claim 1, wherein said support plate comprises homogenizing recesses between said recesses.

8. A sample support for receiving biological and/or chemical samples, comprising:
   a flat support plate of plastic material comprising a plurality of recesses, wherein a support core of a higher-melting material is embedded in said flat support plate, said support core surrounding said recesses, wherein the diameter of said support core is larger than the diameter of said recesses,
   wherein said support core is enclosed by said plastic material at least in the area of said recesses of said support plate, wherein said sample support is designed as a chip, and said recesses are channels.

9. A sample support for receiving biological and/or chemical samples, comprising:
   a flat support plate of plastic material comprising a plurality of recesses, wherein a support core of a higher-melting material is embedded in said flat support plate, and wherein:
   said support core is a metal plate with openings corresponding to said recesses,
   said openings of said support core are not exposed to said recesses,
   the dimensions of said openings of said support core are larger than those of said recesses of said support plate, and
   the wall thickness of said recesses in the region of said support core is in the range between about 0.1 to 0.7 mm.

* * * * *